(12) United States Patent
Weng et al.

(10) Patent No.: US 9,439,874 B2
(45) Date of Patent: Sep. 13, 2016

(54) FOOD COMPOSITION FOR NOURISHING, MAINTAINING AND CULTIVATING A VARIETY OF STEM CELLS AND A METHOD FOR MANUFACTURING THE SAME

(71) Applicant: THE WRITER OF RESVERATROL BIOTECH R&D CO., LTD., Kinmen County (TW)

(72) Inventors: Ming-Chia Weng, Kinmen County (TW); Chi-Ming Wu, Kinmen County (TW)

(*) Notice: Subject to any disclaimer, the term of this patent is extended or adjusted under 35 U.S.C. 154(b) by 610 days.

(21) Appl. No.: 13/647,837

(22) Filed: Oct. 9, 2012

(65) Prior Publication Data

US 2013/0259893 A1    Oct. 3, 2013

(30) Foreign Application Priority Data

Mar. 30, 2012    (TW) .............................. 101111210 A

(51) Int. Cl.
| | |
|---|---|
| *A61K 36/48* | (2006.01) |
| *A61K 31/05* | (2006.01) |
| *A61K 36/258* | (2006.01) |
| *A61K 31/704* | (2006.01) |
| *A61K 36/704* | (2006.01) |
| *A61K 36/45* | (2006.01) |
| *A61K 31/715* | (2006.01) |
| *A61K 36/537* | (2006.01) |
| *A61K 36/03* | (2006.01) |
| *A61K 36/05* | (2006.01) |
| *C12N 5/00* | (2006.01) |

(52) U.S. Cl.
CPC .............. *A61K 31/05* (2013.01); *A61K 31/704* (2013.01); *A61K 31/715* (2013.01); *A61K 36/03* (2013.01); *A61K 36/05* (2013.01); *A61K 36/258* (2013.01); *A61K 36/45* (2013.01); *A61K 36/48* (2013.01); *A61K 36/537* (2013.01); *A61K 36/704* (2013.01); *C12N 5/0018* (2013.01); *C12N 2500/76* (2013.01)

(58) Field of Classification Search
None
See application file for complete search history.

(56) References Cited

PUBLICATIONS 2002 http://stemcells.nih.gov/info/basics/pages/basics1.aspx.*

* cited by examiner

*Primary Examiner* — Catheryne Chen
(74) *Attorney, Agent, or Firm* — Meagher Emanuel Laks Goldberg & Liao, LLP

(57) ABSTRACT

A food composition for nourishing, maintaining and cultivating a variety of stem cells, the food composition includes grape skin or *polygonum cuspidatum* root extract; *pseudoginseng* extract; cooked *polygonum multiflorum* thunb extract; *salvia miltiorrhiza* bunge extract; blueberry extract; bitter melon extract; soybean extract; *ginseng* extract; *rhodiola* extract; yam extract; licorice extract; *pueraria* extract; brown algae extract; green algae extract; chuanxiong extracts, Green tea extract; apple extract; leek seed extract; wolfberry extract; pot marigold extract; *ganoderma lucidum* extract; caterpillar fungus extract; *agaricus* blazei murill extract; cistanche deserticola extract; mushroom extract; beer yeast; flaxseed oil powder; and vitamin.

3 Claims, 8 Drawing Sheets

| | Grape skin / Polygonum cuspidatum root | Pseudo-ginseng | Salvia Miltiorrhiza |
|---|---|---|---|
| The recipe is a effective component that can use for nourishing, maintaining and culturing the stem cells | Ⓐ Resveratrol<br>Ⓑ PPARsactive agent | Ⓐ Resveratrol<br>Ⓑ PPARsactive agent<br>Ⓒ Total Saponins of Panax Notoginseng<br>Ⓓ Quercetin | Ⓐ Resveratrol<br>Ⓑ PPARsactive agent<br>Ⓒ Tanshinol<br>Ⓓ Tanshinone<br>Ⓔ Protocatechuic acid |
| Hematopoietic stem cells | | Ⓒ | ⒸⒹ |
| Mesenchymal stem cells | ⒶⒷ | ⒷⒸⒹ | ⒷⒸⒹⒺ |
| Neural stem cells | ⒶⒷ | ⒶⒷⒸ | ⒶⒷⒸⒹⒺ |
| Retinal stem cells | Ⓐ | ⒶⒸⒹ | Ⓐ∨ |
| Endothelial precursor stem cells | Ⓐ | Ⓐ Ⓒ ∨ | ⒶⒸⒹ∨ |
| Skin stem cells | Ⓐ | Ⓐ | Ⓐ |
| Cochlear stem cells | Ⓐ | Ⓐ | Ⓐ |
| Cancer stem cells | ⒶⒷ | ⒶⒷ | ⒶⒷ |

FIG.3A

| Polygonum multiflorum Thunb | Blueberry | Ginseng | Pueraria | Rhodiola rosea | Liquorice | Brown alga | Green alga |
|---|---|---|---|---|---|---|---|
| Resveratrol | Resveratrol | PPARs active agent | PPARs active agent | PPARs active agent | PPARs active agent | PPARs active agent | PPARs active agent |
| PPARs active agent | PPARs active agent | Ginseng saponins | Puerarin | Salidroside | Glycyrrhizin | Fucoidan | Phycocyanin |
| Serum containing traditional Chinese medicine | Anthocyanin | Ginseng polysaccharide | | Rhodiola polysaccharides | | Sodium alginate | DHA |
| | Gallogen | Dammarane glycosides HSSF | | Catechin | | | |
| | Pterostilbene | | | | | | |
| Ⓐ | Ⓐ | ⒸⒹⒺ | Ⓒ | ⒸⒹⒺ | | Ⓒ | Ⓒ |
| ⒷⒸ | Ⓑ | ⒷⒸⒺ | ⒷⒸ | ⒷⒸⒺ | Ⓑ | ⒷⒹ | Ⓑ |
| Ⓐ Ⓑ | Ⓐ Ⓑ | ⒷⒸⒺ | ⒷⒸ | ⒷⒸ | Ⓑ | ⒷⒹ | Ⓑ |
| Ⓐ | Ⓐ Ⓒ | | Ⓒ | Ⓔ | | | Ⓓ |
| Ⓐ Ⓐ | Ⓐ | Ⓒ Ⓔ | | ⒸⒹⒺ | Ⓒ | Ⓓ | |
| Ⓐ | Ⓐ | Ⓔ | | | | | |
| Ⓐ | Ⓐ | | | | | | |
| Ⓐ Ⓑ | Ⓐ Ⓑ | Ⓑ | Ⓑ | Ⓑ | Ⓑ | Ⓑ | Ⓑ |

FIG.3B

| Bitter melon | | Soybean | | Yam | | Glossy ganoderma | | Mushroom | | Lycium chinensis | | Ligusticum wallichii | | Glutinous rehmannia |
|---|---|---|---|---|---|---|---|---|---|---|---|---|---|---|
| PPARsactive agent | | PPARsactive agent | | PPARsactive agent | | Amino - adipic acid | | Amino - adipic acid | | | | | | |
| Triterpene | | | | Dioscin | | Ganoderma lucidum polysaccharides | | Lentinan | | Lycium Barbarum polysaccharides | | Ligustrazine | | Rehmannia glutinosa polysaccharide |
| | | | | | | Ganoderma lucidum spores | | Carnosine | | Taurine | | Sodium ferulate | | |
| | | | | | | Triterpene | | | | Zeaxanthin | | | | |
| | | | | Ⓑ | Ⓒ | Ⓒ | | | | Ⓒ | | Ⓒ | Ⓓ | Ⓒ |
| Ⓑ | | Ⓑ | | Ⓑ | | | | | | Ⓒ | | Ⓒ | Ⓓ | Ⓒ |
| Ⓑ | | Ⓑ | | | | Ⓒ | Ⓓ | | | Ⓒ | Ⓓ | Ⓒ | Ⓓ | Ⓒ |
| | | | | | | Ⓐ | Ⓓ | Ⓐ | | Ⓒ | Ⓓ Ⓥ | Ⓒ | Ⓓ | |
| | | | | | | | | | | Ⓥ | | | | Ⓒ |
| | | Ⓑ | | Ⓑ | | Ⓔ | | | | | | | | |
| Ⓑ Ⓒ | | | | | | | | | | | | | | |

FIG.3C

| Green tea | Cordyceps sinensis | Apple | Cistanche salsa | Agaricus blazei | Chinese chive seed | Flaxseed |
|---|---|---|---|---|---|---|
| PPARs active agent | | | | | | PPARs active agent |
| Catechin | Cordyceps polysaccharide | Quercetin | Serum containing algae | Agaricus blazei polysaccharide | Taurine | DHA |
| | | | | | | |
| | | | | | | |
| C | V | | | C | | |
| B | V | C | C | | | |
| B | V | C | V | | | B |
| C | | | | | C | B C |
| | | | | | | C |
| C | V | | | | | |
| | | | | C | | |
| B | | | | | | B |

```
┌─────────────────────────────────────────────────────────┐
│ Adding appropriate amount of water into Hydroxy          │
│ C-beta-cyclodextrin (HP-β-CD) and brown algae extracts   │
│ (sodium alginate), then dissolving them completely by a  │
│ magnetic stirring device                          ~S1    │
└─────────────────────────────────────────────────────────┘
                                                    S2
   ┌──────────────────────────────────────────────────────────┐
   │ Taking appropriate amount of resveratrol from grape       │
   │ skins/polygonum cuspidatum root extracts, dissolving      │
   │ following extracts by using appropriate amount of         │
   │ anhydrous alcohol, the extract comprising                 │
   │ pseudo-ginseng extracts, cooked polygonum multiflorum     │
   │ extracts, salvia miltiorrhiza bunge extracts, blueberry   │
   │ extracts, balsam pear extracts, soybean extracts,         │
   │ ginseng extracts, rhodiola rosea extracts, chinese yam    │
   │ extracts, liquorice extracts, puerarin extracts, brown    │
   │ algae extracts, green algae extracts, ligusticum          │
   │ chuanxiong hort extracts, green tea extracts, apple       │
   │ extracts, leek seed extracts, matrimony vine extracts,    │
   │ pot marigold extracts, ganoderma spp extracts, cordyceps  │
   │ sinensis extracts, agaricus blazei extracts, cistanche    │
   │ extracts, mushroom extracts, beer yeast (β-1,3/1,6        │
   │ glucan), flaxseed oil powder extracts and vitamin, the    │
   │ dissolved extract being slowly dropped and added into     │
   │ the water solution containing cyclodextrin and sodium     │
   │ alginate, continuing to stir for a period of time,        │
   │ resting these extracts for a period of time, and then     │
   │ filtering out impurities                                  │
   └──────────────────────────────────────────────────────────┘
                                                  S3
┌─────────────────────────────────────────────────────────┐
│ Acquiring a mixed solution by combining (S1) with (S2)   │
│ to obtain a filtrate, the filtrate transferred into a    │
│ petri dish, and storing into refrigerator overnight      │
└─────────────────────────────────────────────────────────┘
                                                  S4
┌─────────────────────────────────────────────────────────┐
│ Taking out the mixed solution, which is frozen, from the │
│ refrigerator in the next day, drying it by using spray   │
│ drying or vacuum drying for 12 hours tomake them as      │
│ trituration of loose bulk materials so that the food     │
│ recipes in form of powder of inclusion complex is        │
│ obtained                                                 │
└─────────────────────────────────────────────────────────┘
                                                  S5
┌─────────────────────────────────────────────────────────┐
│ Using an excipient to make the powdered food recipes     │
│ into type of capsule, tablet, ingot and aluminum foil    │
│ bag, wherein each of the capsule type, the tablet type,  │
│ the ingot type and the aluminum foil bag type            │
└─────────────────────────────────────────────────────────┘
```

FIG.4

FOOD COMPOSITION FOR NOURISHING, MAINTAINING AND CULTIVATING A VARIETY OF STEM CELLS AND A METHOD FOR MANUFACTURING THE SAME

FIELD OF THE INVENTION

The present invention relates to a food composition for nourishing, maintaining and cultivating a variety of stem cells and a method for manufacturing the same, and more specially relates to the food composition for proliferation, activation, repairing, nourishing of the stem cells and a method for manufacturing the same.

BACKGROUND OF THE INVENTION

The various pharmaceutical factories in the current world are doing a lot of efforts to induce stem cells to convert into the tissues or cells as desires, and it thus leads this as one of the most attracting major subject for all institutes in stem cell research Area in the world. The United Stated has conducted many researches that combines food which has stimulating single stem cell. The resveratrol attracts more attention especially after Dr. SeLuzi Nujo of France in 1991 found that there are resveratrol in the red wine, and then Dr. Pezzuto, University of Illinois, declared resveratrol is effective of inhibiting the three main stages of initiation, promotion and progression of the tumor. In the following study, people found that resveratrol have some inhibitory effects on 29 kinds of cancer/tumor. They also found if resveratrol is used along with the chemotherapy and radiotherapy, the curative effect is double than any single use. In past two years, people's newest study has found that resveratrol surprisingly could uniquely inhibit the cancer stem cells. From 2000, people found that resveratrol used in the animal experiment could prolong the 30-75% of life of nematodes, drosophila, African Carp (a most short-lived fish) and mouse by starting the animal longevity gene called Sirtuin. The resveratrol also is amazing to make the aging skin younger. Over 3000 research literatures in the world declares the resveratrol could improve people in functions of antioxidation, antibiosis, anti-virus, eliminating toxin, anti-inflammatory, anti-obesity, adjusting the immune function, prevention of cardiovascular disease, protecting the central nervous system, improving the eye sight, reducing the high blood pressure, high cholesterol and high blood sugar. It also could activate the estrogenic hormone, has bipartite regulatory effects to delay and relieve the female climacteric syndrome, and prevents/treats the osteoporosis and arthritis. The study found that the resveratrol could process a lot of chemical binding reactions and impact a lot of specifically major gene, as shown in FIG. 1 and FIG. 2.

There exists a problem, called molecular dissolution after taken, for an application of resveratrol. The resveratrol, with a molecular formula $C_{14}H_{12}O_3$, a molecular weight 228.25, a melting point 256-257° C. and a sublimation point 261° C., is a colorless needle-shaped crystal which is hardly soluble (slightly soluble) in water, but soluble in ethyl ether, chloroform, methanol, ethanol, acetone, acetic ether and other organic solvents with strong nonpolarity. The resveratrol is hardly absorbed if being swallowed with water, but is well absorbed with red wine, because of alcohol content in red wine, and it thus solves the mystery of French Paradox.

There are called cis & trans structures and its transformation. The resveratrol is with its extraordinary effect only if it is in a trans-resveratrol structure but is with not any effect in the cis-resveratrol structure. Natural resveratrol mainly exists in trans-resveratrol structure, and it turns into the cis-resveratrol structure under UV irradiation. Resveratrol exists in 72 plants and can be synthesized chemically. Resveratrol extracted from natural plant is generally the mixture of cis & trans structures, whose proportion varies by different plants. However, cis-resveratrol as the parent compound of 1,2-viniferins has never been examined in grape extracts.

The so-called problem of high absorption rate and low bioavailability is explained as follows. If the resveratol is taken orally, it generates a very special phenomenon different from general compounds, which brings a great challenge for its application as a drug. According to the results obtained from pharmacokinetics studies, whether to be taken orally or injected, the resveratrol will be absorbed by human body rapidly (within 10 min) and enter the circulation (blood) system. After that, the concentration of resveratrol in blood rises greatly to reach its peak in about 1 to 2 hours and declines greatly after that. In about 4 hours, resveratrol can't be detected in the blood, and after 4 hours, about 77% resveratrol is detected in the urine. This regrettable phenomenon is called as "high absorption rate and low bioavailability"

Another problem called problem of storage and processing is that during processed or after made into food, resveratrol shall be provented from exposure to the air to against oxidization. Trans-resveratrol will degrade seriously after preserved under a low temperature of 4° C. over 1 year, so it can't be preserved in ice overstepping the time limit.

The so-called absorption route of resveratol is that there are two functional routes after resveratrol being taken orally and entering human body. The functional routes includes: a sirt1-dependent route, taking effect through activating sirt1 gene and whose effect is closely linked with sirt1 gene; and a sirt1-independent route, taking effect without stimulating sirt1 gene.

As discovered in the latest studies, if low-dose resveratrol is taken orally, it will take the sirt1-dependent route, which will activate sirt1 gene and then release sirt1 protein to change, including enhance or weaken, the functions of P53, FOXO, $NF_\kappa B$ and other genes. On the other hand, if high-dose resveratrol is taken orally, it will take the sirt1-independent route, the functions of which are not concerned with sirt1. It is a wrong cognition of general people that a higher dose generates better effect.

Thus, it is an issue regarding how to appropriately use dose of resveratrol.

SUMMARY OF THE INVENTION

Therefore, the object of the present invention provides a food composition for nourishing, maintaining and cultivating a variety of stem cells including hematopoietic stem cells, mesenchymal stem cells, endothelial precursor stem cells, neural stem cells, retinal stem cells and cochlear stem cells and a method for manufacturing the same, based on the consideration that the proliferation and activation of the stem cells according to the above mentioned drug test report, also indicating that it is only allowed to activate normal stem cells at the present time and the cancer stem cells may also be activated after activation of the normal stem cells. Meanwhile, there are also some restrictions and difficulties of the main ingredient resveratrol in application.

The food composition for nourishing, maintaining and cultivating a variety of stem cells and a method for manufacturing the same of the present invention is advantageous as follows.

(I) Based on the basic theories of the compound foods and the test results for all food combination materials, the present invention is enabled to effect for nourishment, maintenance of hematopoietic stem cells, mesenchymal stem cells, neural stem cells, retinal stem cells, skin stem cells, endothelial progenitor stem cells and cochlea stem cells and to inhibit the cancer stem cells.

(II) The secondary ingredients of the present the present invention are composed of agonist of peroxisome proliferator activated receptor (PPARs) and the food materials such as quercetin, catechin and β-glucan, etc. The conjunctive use of one of the element with resveratrol has an additive plus effect than a single element used. The natural extracts containing these elements are applied without interacting with each other to perform its best effect. The present invention is applied together with cyanidin, carotenol and other food materials, based on the principle of "prevention of interactions but performance of the cooperative functions", which is another characteristic of the present invention.

(III) The constituent parts of the present the present invention, including the vitamin, linseed oil powder and beer yeast (containing yeast β-1,3/1,6 glucan) is applied since their cooperative effect if combined, and the other constituent parts are proved to be effect directly or indirectly in animal experiment, in-vitro experiment and in-vivo experiment for stem cell proliferation, activation, repair, moistening and adjustment. Ingredient molecule in the present invention is selected from varied plants with function of nourishment, maintenance and decay for varied in-vivo stem cells but not only aiming at a single stem cell, since it is beneficial to nourish and maintain the varied in-vivo stem cells even though there is only one or two kinds of in-vivo stem cells which is senescent, deteriorative and decreased.

(IV) Constituent parts of the present invention are non-carcinogens. On the contrary, there are documents of the research results prove these constituent parts is effect in cancer prevention, anticancer and cancer therapy. Especially, they are good for the stem cell proliferation, activation, repair, moistening and adjustment but is not helpful or even inhibits for the cancer stem cells.

(V) Resveratrol, the main constituent of the present invention, is a molecule in natural food which has effects on 29 cancers/tumors as discovered by many animal experiments. With regard to its anticancer mechanisms, the most advantageous mechanism is that it can treat the cancer stem cell CD133 molecule, interfere the signal pathway to phosphatidylinositol-3-kinase (PI3K), inhibit the signal pathway of mammalian target of rapamycin (mTOR), slow down the growth of cancer stem cell and inhibit the proliferation of cancer stem cell. Resveratrol can also inhibit the transcription of cancer hTERT gene (telomerase reverse transcriptase), thus to decrease the hTERT mRNA. There is a position for the combination of $NF_\kappa B$ and AP-1 at the startup of hTERT to decrease the activity of hTERT and inhibit the growth of cancer stem cells without destroying the normal stem cells. Resveratrol is the inhibitor of cancer bodyguard $NF_\kappa B$, inhibits the tumor angiogenesis, promotes the in-vitro differentiation of GBM (glioblastoma multiforme) stem cell with positive CD133 to decrease its ability to form tumors in the experimented animal body, and inhibits the Interleukin-8 (IL-8) expression of cancer stem cell. The main constituent of the present invention is the natural product discovered with the most effective capability to treat the cancer stem cells.

(VI) The constituent of the present invention including ginseng, matrimony vine, herba rhodiolae, radices rehmanniae, *ganoderma lucidum*, gordyceps *sinensis*, brown algae, green algae, mushroom, and *agaricus* blazei murill (ABM), beer yeast (β-1,3/1,6 glucan) the present invention are all polysaccharide containing sugar chain, which is used for treating the cancer cells with excellent effect in these 20 years in Japan, since the sugar chain can generate the phenomenon of carbohydrate antigens on the surface of the cancer cells, in which a cell without carbohydrate antigen is a normal cell free of cancer. Low-molecule *agaricus* blazei murill (LMPAB) can down regulate the expression of RNA and mRNA of hTERT, decrease the activity of telomerase and inhibit the growth of tumor stem cell. In addition, the root of red-rooted *salvia*, catechin and resveratrol are called as the $NF_\kappa B$ inhibitor of cancer bodyguard, which will slow down the growth of cancer stem cell without affecting the growth and survival of normal stem cells. Triterpenes of bitter gourd can block the signal pathway by the cancer cell to the core thus to inhibit the proliferation of the cancer stem cells.

(VII) Food formula provided by the present invention for nourishment, maintenance of varied stem cells is extracted from purely natural ingredients, which is edible for human body without side effect.

(VIII) The present invention solves the restrictions and difficulties of resveratrol in application, changes the disadvantages into advantages, and furthermore enables resveratrol to have addition-multiplication effect via the cooperative effect and exerts a biological.

The solutions the present invention solve the conventional restrictions and difficulties of resveratrol in application as follows.

1. Solutions to the problem of molecular dissolution after being taken. (1) Embed resveratrol molecule by Hydroxypropyl-β-Cyclodextrin (HP-β-CD) to improve its solubility. Indicates in studies, the hardly soluble drugs embedded by HP-β-CD not only increases the solubility but also advances the bioavailability and stability thereof as well. After test, using HP-β-CD to embed the resveratrol is proved extremely good by the determination of the inclusion rate.

(2) The other extracts in the constituents containing resveratrol such as (ripe) *polygonum multiflorum* extracts, *pseudo-ginseng* extracts, root of red-rooted *salvia* extracts and blueberry extracts shall be included, or otherwise the resveratrol shall be taken with red wine, wine, deep-sea fish oil or vegetative ω3, which can also solve the problems of solubility and stability.

2. Solutions to the problem of cis & trans structures and transformation of resveratrol. Trans-resveratrol is very instable and will transform into cis-resveratrol under the UV irradiation. After its aqueous solution (pH1-7) kept in dark place for 28 day, 4.7% of the trans-resveratrol will transform into cis-resveratrol. Low water solubility and poor stability under UV irradiation restrict the all-purpose application. Therefore, HP-β-CD is used to embed the resveratrol into inclusion compound. Under the irradiation of UV analyzer (136 μw/cm$^2$) in experiment, if compared with the unembedded resveratrol, the isomerization of the embedded trans-resveratrol slows down and the unembedded resveratrol quickens up isomerization. Moreover, the food formula packaged by capsule solves the problems of oxidization misgivings and stability.

3. Solutions to the problem of high absorption rate and low bioavailability of resveratrol. If taken orally, high absorption rate and low bioavailability problem will occur in resveratrol, which is a very special phenomenon distinct from general compounds. This brings a great challenge for its drug application. Discovered from the studies, the co-existence of trans-resveratrol with some antioxidants will prolong the residence time of resveratrol in human body. Thus the present invention selects the antioxidant food materials having that kind of ingenious relationship with resveratrol, such as cyanidin and procyanidin which prolong the residence time of trans-resveratrol in human body. Moreover, in the discover of biologists and physicians, the co-existence of trans-resveratrol and a certain substance can enhance greatly the effect of trans-resveratrol as indicated in guidance file of National Institutes of Health (USA) which explains clearly that joint use of trans-resveratrol and the antioxidant such as cyanidin, indole or green tea catechin generates cooperative effect. Reported by a periodical of Nature in November, 2006 and Cell in December 2006 respectively, the resveratrol could reduce the acetylation reaction of PGC-1α ferment, enhance the active effect of PGC-1α and combine with PPARs active agent to present an addition-multiplication activation effect of PPAR molecule. Experiment by clinical group of National Health Research Institutes, Taiwan also confirms that resveratrol has effect of transformation coenzyme similar to RXR and is able to activate PPAR molecule. Explained clearly in the papers published in 2007, the joint use of trans-resveratrol and the antioxidant quercetin had cooperative effect. Papers of joint study by Professor Walter Wichgar in University of Louisville (USA) and Professor Flogny of innovation research institute (Czechoslovakia) explains that the joint use of trans-resveratrol and glucan has cooperative effect. It can prolong the half-life period of resveratrol in human body, increase the area under the curve, promote the maximum blood concentration of resveratrol, reduce its clearance rate, enhance the bioavailability and exert the pharmacological action of resveratrol, by applying, for example, the blueberry extracts rich in cyanidin and procyanidin, apple extracts rich in quercetin, green tea extracts rich in catechin, beer yeast β glucan rich in β-1,3/1,6 glucan; (ripe) *polygonum multiflorum* extracts, grape skin or *polygonum cuspidatum* root extracts, *pseudo-ginseng* extracts and blueberry extracts rich in resveratrol and containing PPARs active agent; *momordica charantia* extracts, soybean extracts, the root of kudzu vine extracts, herba rhodiolae extracts, liquorice extracts, *ginseng* extracts, brown alga extracts, green alga extracts, rhizoma dioscoreae extracts rich in PPARs active agent; and with the multiphasic liposomes.

4. Solutions to the problem of processing and storage of resveratrol. Although the chemically synthesized resveratrol is inexhaustible in supply, its effect is much poor than that extracted from natural products, which is effective without side effect. The optimal solution for powders and capsules is to apply naturally resveratrol prepared and processed as raw material to prevent from being exposed in the and sunlight after manufactured as raw material or as products, not stored under a condition of 4 over 1 year to prevent from serious degeneration and embedded with HP-β-CD.

5. Solutions to the problem of absorption route of resveratrol. There are two absorption routes after resveratrol taken orally: sirt1-dependent route and sirt1-independent route, wherein low-dose resveratrol will take the sirt1-dependent route, which is closely linked with human activity, and high-dose resveratrol in condition of major diseases or cancer will take the sirt1-independent route. General food formula selects a low dose about 80-150 mg. Oral taking is the most common path, since it is convenient in use and acceptable by the masses. However, unsatisfactorily, Oral taking generally is not as significant effective in human body as in animal experiment if it doesn't cooperate with the cooperative substance. In oral taking path, the dose of drugs reaching the target infected cells is hard to be controlled accurately since the drug has to pass through intestines and stomach digestive system, first pass metabolism and blood circulation system, thus to make the drug dose too much or too little and fail to achieve the desired effect. Low dose of 80-150 mg in the present invention mainly takes the sirt1-dependent route. If required by the eaters' body, the dose can be increased to take the sirt1-independent route suitable to different persons. Taking sodium alginate as the carrier, the resveratrol embedded into inclusion by HP-β-CD as capsule in slow-release technology can prolong the residence time of formula in body and achieve the target controlled release effect.

6. Solutions to the problem of using dose of resveratrol. According to an animal experiment for 28 consecutive days with a dose of 30-3000 mg, it is considered that a dose within 2000 mg is safe and has no side effect for the safety in heredity or deformity for pregnant mice and fetus mice experiment. However, what dose is effective for human body? As regard to this problem, some scientists suggest to convert based on the amount in animal experiment to the amount in human body (in unit of body weight). While, some suggest to apply the dose-dependent type according to the animal experiment of related symptoms. Dr. Xi Zhao-Wilson points out that until now studies on the human body can't determine the optimum dose of resveratrol, and suggests taking in high-quality resveratrol from daily food for a good health. Ward Daean considers that, although the optimum dose of resveratrol in human body is not determined, the reasonable dose of human body is significant within the following scope: 1-10 mg/day for prevention and anti-aging and 10-100 mg/day for curing. It is recommended that a higher dose is used for supplementary control of all cancers.

Professor Sinclair in Harvard University (USA) estimates that an adult with a body weight of 60 kg shall take in 1344 mg trans-resveratrol each day to achieve the same effect of longevity and anti-aging effect as in the mice experiment. However, since Mr. Sinclair involves a complicated business operation, his estimation is accused of lots of queries from the academic world immediately. In the year 2007-2009, research papers about dose required for human body provides some applicable data for all experiments, wherein 80-150 mg is the mainstream dose obtained the most support. This formula takes 80-150 mg as the effective dose and set 1500 mg as the upper limit of the safe dose in consideration of the safety.

BRIEF DESCRIPTION OF THE DRAWINGS

The structure and the technical means applied by the present invention for achieving the above and other objects can be best understood by referring to the following detailed description of the preferred embodiments and the accompanying drawings.

The FIG. 1 is a block diagram that resveratrol can make many chemical reactions to combine the reactive molecules.

Figure 1:
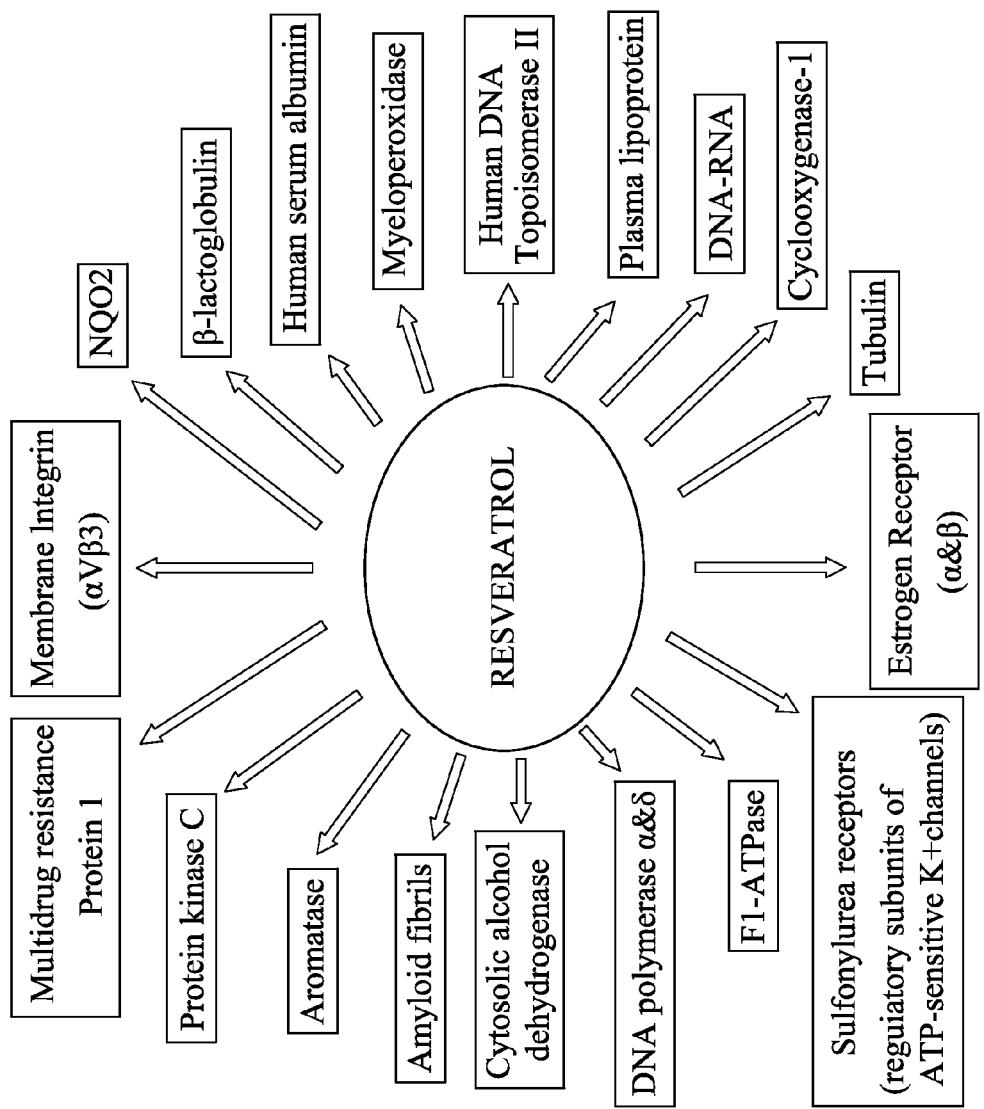
Figure 2:
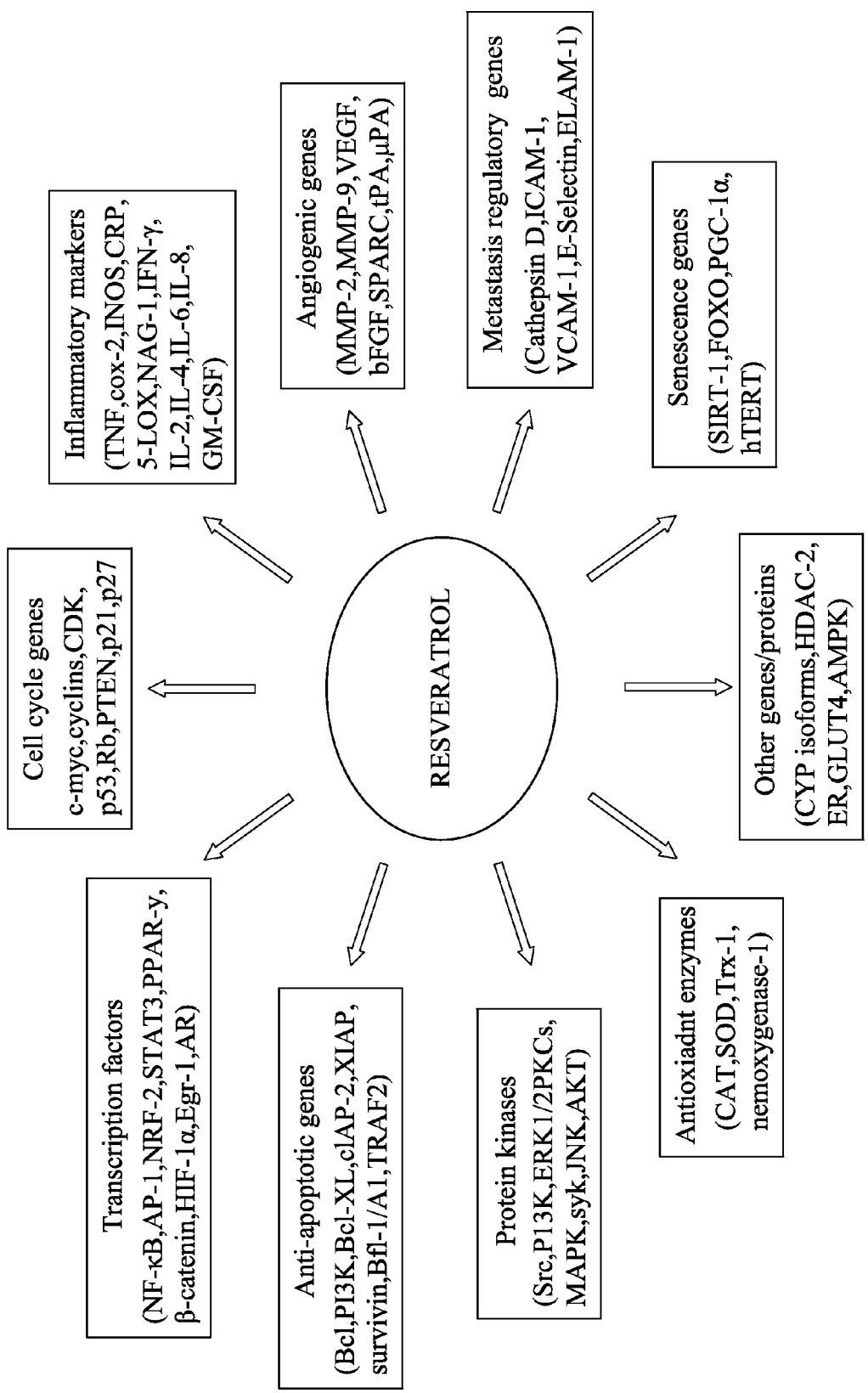

The FIG. 2 is a block diagram that the present invention shall be influenced by resveratrol.

Figure 3:
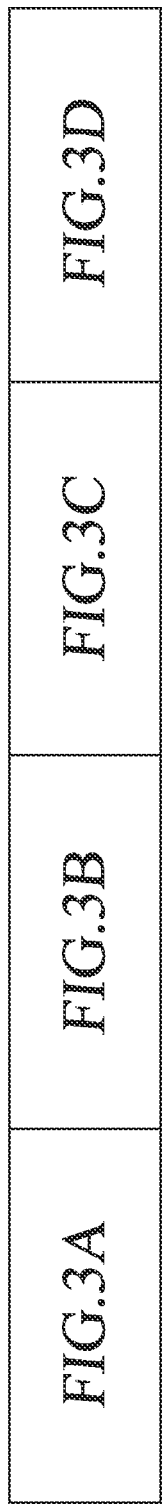

The FIG. 3 shows the orientation of FIG. 3A, 3B, 3C and 3D which are block diagrams showing that the present invention proven in animals testing and human testing can nourish, maintain and repair the stem cells.

The FIG. 4 is flow diagram of manufacturing method of the present invention.

DETAILED DESCRIPTION OF THE PREFERRED EMBODIMENTS

The detailed description of the invention which follows is made with reference to the drawings and in terms of a preferred embodiment of the invention. The detailed description is not intended to limit the scope of the present invention, and the only limitations intended are those embodied in the claims hereto.

Embodiment 1: Composition of food composition for nourishment, maintenance and cultivation of varied stem cells. In a preferred embodiment, the food composition for nourishment, maintenance and cultication of varied stem cells is in form of powder. Each unit of ingredient is composed of 80-150 mg grape skin or *polygonum cuspidatum* root extracts, 30-60 mg *ginseng* extracts, 45-90 mg *pseudo-ginseng* extracts, 50-95 mg wolfberry extracts, 45-90 mg the root of kudzu vine extracts, 35-70 mg *ligusticum* wallichii extracts, 35-65 mg the root of kudzu vine, 40-80 mg herba rhodiolae extracts, 25-50 mg brown algae extracts, 25-45 mg green algae extracts, 25-45 mg apple extracts, 20-35 mg pot marigold extracts, 20-40 mg green tea extracts, 20-35 mg *ganoderma lucidum* extracts, 20-35 mg blueberry extracts, 10-30 mg caterpillar fungus extracts, 10-30 mg broomrape extracts, 10-30 mg leek seed extracts, 10-40 mg beer yeast (yeast β-1,3/1,6 glucan), 5-20 mg (ripe) *polygonum multiflorum* extracts, 5-20 mg licorice extracts, 5-20 mg *agaricus* blazei murill extracts, 5-20 mg rhizome dioscoreae extracts, *momordica charantia* extracts, 5-20 mg soybean extracts, 5-20 mg mushroom extracts, 5-20 mg linseed oil powder and 5-10 mg vitamin. The ingredient can also includes spice, fruit juice powder and HP-β-CD, which can enhance its palatability, promote the food solubility, increase the UV stability and improve the food bioavailability.

The detailed description of the invention in the follows is made with reference to the drawings and in terms of a preferred embodiment of the invention. The detailed description is not intended to limit the scope of the present invention, and the only limitations intended are those embodied in the claims hereto. The food composition comprises grape skin or *polygonum cuspidatum* root extracts, *pseudo-ginseng* extracts, (ripe) *polygonum multiflorum* extracts, the root of red-rooted *salvia* extracts and blueberry extracts are rich in resveratrol, which contains the molecule for chemical binding reaction to affect the gene acting on human body and achieve the effect of varied stem cells proliferation, activation, repair, nourishment and adjustment. The root of red-rooted *salvia* extracts and blueberry extracts contain both resveratrol and PPARs active agent. The *ginseng* extracts, herba rhodiolae extracts, *momordica charantia* extracts, soybean extracts, rhizoma dioscoreae extracts and licorice extracts are rich in PPARs; licorice extracts are rich in PPARs active agent and puerarin; brown algae extracts are rich in PPARs active agent, puerarin and sodium alginate; green algae extracts are rich in PPARs active agent, phycocyanin and DHA. PPARs is a kind of transcriptional factor depending on ligand activation and belongs to the nuclear hormone receptor family. It includes three isomers, i.e. PPARα, PPARδ/δ and PPARγ, which will bind with retinoids to form heterodimers and activate after binding with the ligand (PPARs active agent), thus to bind in the PPAR response area on the upper stream of the start point of target gene transcription and activate the target gene for transcription. In addition to that the composite molecule with PPARs active agent is able to wake up and activate the functions of cells, the PPARδ/PPARγ may participate in the regulation on proliferation and differentiation of neural stem cells. PPARγ can enable the mesenchymal stem cells to differentiate into fat cells, shorten the differentiation process and promote the differentiation efficiency. Stem cell proliferation, activation and repair by resveratrol are achieved through PPARs sometimes. Stem cell proliferation, activation and repair by resveratrol can also be achieved through puerarin, fucoidan, sodium alginate and phycocyanin, for example that the *ligusticum* wallichii extracts contain ferulic acid and ligustrazine, green tea extracts contain catechin, apple extracts contain quercetin, leek seed extracts contain ethylamine sulfonic acid, wolfberry extracts, *ganoderma lucidum* extracts, caterpillar fungus extracts, *agaricus* blazei murill extracts, mushroom extracts and β-glucan contain polysaccharide, wherein any of catechin, quercetin and β-glucan if activated with resveratrol will have an additional plus effect. Sodium ferulate can accelerate the hemopoietic stem cell to repair the damaged kidney, ligustrazine has a certain mobilization effect on the hemopoietic stem cell, which can improve the microenvironment of bone marrow and promote the hemopoietic reconstitution of bone marrow. Sodium ferulate can induce the mesenchymal stem cells to differentiate to the nerve cells and has the function of nerve protection and neurogenesis enhancement. Ligustrazine can enhance the proliferation of mesenchymal stem cells, induce the mesenchymal stem cells to differentiate into neuron-like cells, promote the proliferation of neural stem cell at the subventricular zone (SVZ) induced by focal cerebral ischemia, promote the proliferation of endogenous neural stem cell in dentate gyrus of hippocampus of ischemia-reperfusion injury rats. Both ferulic acid and ligustrazine can significantly accelerate the regeneration and prolongation of axon in retinal ganglial cells. Catechin can accelerate the proliferation and differentiation of hemopoietic stem cell and hemopoietic progenitor cell, which can accelerate the growth of human hair follicle and promote the proliferation of human dermal papilla cells through affecting the cell cycle. Quercetin can accelerate the proliferation and osteogenic differentiation of mesenchymal stem cells, promote the bone fracture healing and prevent against osteoporosis. Meanwhile, quercetin can promote the proliferation of human retinal pigment epithelial cell (RPE), inhibit the damage of oxidative stress to RPE and prevent against apoptosis. Ethylamine sulfonic acid can promote the proliferation of neural stem cell after focal cerebral ischemia and prevent against apoptosis in neuronal cells due to hematencephalon, which has a certain protection function on nerve cells. Ethylamine sulfonic acid can induce the cell differentiation of mesenchymal stem cells to photoreceptor cell or rhodopsin. *Lycium barbarum* polysaccharide can accelerate the proliferation of hematopoietic stem cells from bone marrow and promote the granulocyte differentiation of colony forming unit of granulocyte and macrophage (CFU-GM). In addition, *Lycium barbarum* polysaccharide can also delay the differentiation of mesenchymal stem cells to endothelial ancestry and induce the mesenchymal stem cells to transform into neuron-like cells. *Lycium chinense* is rich in zeaxanthin, which is the optimum nutrient for eye macular. Meanwhile, *lycium chinense* can protect the retinal ganglion cells, photoreceptor cell and neural stem cell. *Ganoderma lucidum* polysaccharide F3 can promote the proliferation of hemopoietic stem cell and enhance human immunity. Spores of *ganoderma lucidum* can promote proliferation of the cellula adhesiae in damaged spinal cord central canal. Part of the proliferated cells can differentiate into neural stem cells, neuron-like cells, oligodendrocytes and astrocyte-like cells. *Lycium barbarum* polysaccharide has the neuroprotective function to the hippocampus neuron cell damage induced by β amyloid protein (Alzheimer's disease). Spores of *ganoderma lucidum* have the recovery function to retinal photoreceptor cells damage. Caterpillar fungus can promote the proliferation of hemopoietic stem cell, accelerate the differentiation of sclerocyte and bone histogenesis of the mesenchymal stem cells, reduce the gene expression of osteoclast differentiation factor and induce the committed differentiation of neural stem cells. *Agaricus blazei murill* (ABM) polysaccharide can promote the proliferation of hemopoietic stem cell and hemopoietic progenitor cell, etc. The food formula for nourishment, maintenance and culture of varied stem cells can be powdery, granule or liquid type. The unit can be a capsule, a tablet, a pastille, a packing bag or a packing bottle. Daily dose can be 1-6 units. Moreover, an excipient or carrier acceptable in pharmaceuticals can be included and selected from the group composed of flavoring agent, sweetener, preservative, chelating agent, penetrating agent, lubricant, tablet adjuvant, colorant, moisturizing agent, binder as well as the medicine compatible carrier.

Embodiment 2: Manufacturing method of food formula for nourishment, maintenance and cultivation of varied stem cells. Please refer to FIG.4 of the manufacturing method of food composition for nourishment, maintenance and culture of varied stem cells, including:

S1, adding appropriate amount of water into Hydroxy C-*beta*-cyclodextrin (HP-β-CD) and brown algae extracts (sodium alginate), then dissolving them completely by a magnetic stirring device;

S2, taking appropriate amount of resveratrol from grape skins/*polygonum cuspidatum* root extracts, dissolving following extracts by using appropriate amount of anhydrous alcohol, the extract comprising *pseudo-ginseng* extracts, cooked *polygonum multiflorum* thunh extracts, *salvia* miltiorrhiza bunge extracts, blueberry extracts, balsam pear extracts, soybean extracts, *ginseng* extracts, *rhodiola rosea* extracts, chinese yam extracts, licorice extracts, puerarin extracts, brown algae extracts, green algae extracts, *ligusticum* chuanxiong hort extracts, green tea extracts, apple extracts, leek seed extracts, wolfberry extracts, pot marigold extracts, *ganoderma* spp extracts, caterpillar fungus extracts, *agaricus* blazei murill extracts, cistanche extracts, mushroom extracts, beer yeast (β-1,3/1,6 glucan), flaxseed oil powder extracts and vitamin, the dissolved extract being slowly dropped and added into the water solution containing cyclodextrin and sodium alginate, continuing to stir for a period of time, resting these extracts for a period of time, and then filtering out impurities;

S3, acquiring a mixed solution by combining S1 with S2 to obtain a filtrate, the filtrate transferred into a petri dish, and storing into refrigerator overnight;

S4, taking out the mixed solution, which is frozen, from the refrigerator in the next day, drying it by using spray drying or vacuum drying for 12 hours tomake them as trituration of loose bulk materials so that the food composition in form of powder of inclusion compound is obtained;

S5, using an excipient to make the powdered food composition into type of capsule, tablet, ingot and aluminum foil bag, wherein each of the capsule type, the tablet type, the ingot type and the aluminum foil bag type.

Percentages of all ingredients in this food composition are as follows:

1. Resveratrol is in weight of about 42% of grape skin or *polygonum cuspidatum* root, *pseudo-ginseng* extracts, (ripe) *polygonum multiflorum* extracts, the root of red-rooted *salvia* extracts and blueberry extracts.
2. PPARs agonist is in weight of about 28% of *ginseng* extracts, the root of kudzu vine extracts, herba rhodiolae extracts, brown algae extracts, green algae extracts, soybean extracts, rhizoma dioscoreae extracts and licorice extracts.
3. Catechin is in weight of 90% of green tea extracts.
4. Quercetin is in weight of 80% of apple extracts.
5. Polysaccharide (glucoprotein) is in weight of 20% of *ginseng* extracts, wolfberry extracts, herba rhodiolae extracts, radices rehmanniae extracts, *ganoderma lucidum* extracts, caterpillar fungus extracts, mushroom extracts, ABM extracts, beer yeast (β-1,3 1,6 glucan).
6. Ginsenosides is in weight of 30% of *ginseng* extracts.
7. *Panax* notoginseng saponins take up 30% of *panax* notoginseng extracts.
8. Lutein is in weight of 80% of pot marigold extracts.
9. Zeaxanthin is in weight of 25% of wolfberry extracts.
10. Tanshinone, danshensu and protocatechuic acid take up 27% of root of red-rooted *salvia* extracts.
11. Ligustrazine and sodium ferulate take up 60% and 30% respectively of the *ligusticum* wallichii extracts.
12. Puerarin is in weight of 70% of root of kudzu vine extracts.
13. Blood serum is in weight of 60% of (ripe) *polygonum multiflorum* extracts and cistanche extracts.
14. Rhodioside is in weight of 30% of the herba rhodiolae extracts.
15. *Ganoderma lucidum* spores take up 30% of *ganoderma lucidum* extracts.
16. Fucoidan and sodium alginate take up 40% respectively of brown algae extracts.
17. Phycocyanin is in weight of 10% of green algae extracts.
18. Ethylamine sulfonic acid is in weight of 70% of leek seed extracts.
19. DHA is in weight of 80% of linseed oil powder extracts and 5% of green algae extracts.

The present invention includes the procedure to add an excipient to make the powdery food composition into capsule, tablet, pastille and packing bag. The prepared mixed solution can also include spice and juice powder. The unit can be a capsule, a tablet, a pastille, a packing bag or a packing bottle. Daily dose can be 1-6 units.

Embodiment 3: Regarding ingredients in the food composition of the present invention. This embodiment is applied to use in single stem cell proliferation, activation, repair, moistening and adjustment. As discovered by the present invention, some ingredients have the function of nourishment, maintenance and cultivation of varied stem cells, which can be developed into a mixture for nourishment, maintenance and cultivation of varied stem cells as well as cancer stem cells inhibition. Its functions have been proved by the previous experiment report. FIG. 3 shows the orientation of FIG. 3A, 3B, 3C and 3D which shows the name thereof, effective molecules and functions of normal stem cells for proliferation, activation, repair, moistening and adjustment in these ingredients and the fact that cancer stem cell inhibited.

Embodiment 4: The food composition with its function of inhibition of cancer stem cells. In 2003, Michael Clarke of Stanford University (USA) and Hilla Singh in Toronto's Hospital for Sick Children (Canada) discovered tumor stem cells in leukaemia, breast cancer and brain tumour. After that, the scientists discovered the tumor stem cells and isolated the carcinogenic cells with the characteristics of stem cells different cancer tissues, e.g. lung cancer, liver cancer, oral cancer, ovarian cancer, prostate cancer, colorectal cancer, pancreatic cancer, melanoma, head and neck cancer. Surface antigens such as CD44+ and CD24− usually adhere on the surface of the cancer cells. In 2004, Dirks and other research teams in Toronto University confirmed that once the surface of human neural stem cell shows the CD133+ glycoprotein surface antigen, new tumors will be developed out. As the research developed, special surface antigens possessed by many cancer cells have been specified gradually. Generally, there is no surface antigen on the surface of normal cells, but there are special surface antigens discovered on the surface of tens of tumors (see Table 1).

TABLE 1

Special surface antigen identified in human cancer stem cells

| Type | Special surface antigens | References |
|---|---|---|
| Acute myeloid leukemia | CD123+, CD44+, CLL-1+, CD25+, CD32+, CD96+, and CD47+ | Proc. Natl. Acad. Sci. 2001 |
| breast cancer | CD44+, CD24−/low | Proc. Natl. Acad. Sci. 100: 3983, 2003. |
| brain tumour | CD133+ | Nature 432: 396, 2004. |
| melanomas | CD20+ | Cancer Res. 65: 9328, 2005. |
| prostate cancer | CD44+, α2β1+hi, CD133+ | Cancer Res. 65: 10946, 2005. |
| multiple myeloma | CD138− | Blood 103: 2332, 2004. |
| Head and neck squamous cell carcinoma | CD44+ | Head Neck. 34: 894, 2012. |
| colon cancer | CD133+ | Nature 445: 106, 2007. |
| colon cancer | CD44+, EpCam+, CD166+ | Proc. Natl. Acad. Sci. 104: 10158, 2007. |
| Pancreatic Cancer | CD44+CD24+ESA+ | Cancer Res. 67: 1030, 2007. |
| Epithelial Ovarian Cancer | CD44+ | Cancer Res. 65: 3025, 2005. |

With regard to the studies on cancer stem cells in Taiwan, in June 2008, the VGHtpe-YangMing Team consisted of the presenter in Stem Cell Laboratory of Taipei Veterans General Hospital and Shih-Hwa Chiou in Institute of Clinical Medicine, National Yang Ming University discovered that the cancer stem cells showed a lot of anti-apoptosis protein and embryonic stem cell regulation proteins. If these specific gene or proteins can be inhibited, the drug resistance and radioresistance of cancer stem cells will disappear, thus the cancer stem cells can be eliminated, and the cancer can be cured once and for all. On Aug. 13, 2008, Yu, Alice Lin-Tsing, the Distinguished Research Fellow and Deputy Director of Genomics Research Center, Academia Sinica and Yu, John, the Distinguished Research Fellow of Institute of Cellular and Organismic Biology, Academia Sinica found out a hexasaccharide (Fucα 1→2Galβ1→3GalNAc β1→3Galα 1→4Galβ1→4Glcβ1) named as Globo H on the surface of breast cancer stem cell, which was seldom expressed in healthy cells. Gb5, which is occurred frequently in embryonic stem cells, was detected in 77.5% breast cancer cells and detected in 62.5% general stem cells. Consequently concluded from the studies, these two glycomolecule existing on the surface of breast cancer cells can be treated as the target to find the antibody drugs or food for breast cancer curing once and for all.

A major breakthrough appeared in the cancer medicine of VGHtpe-YangMing Team of Taiwan on Aug. 6, 2011, Professor Hsei-Wei Wang explained that cancer stem cell was one of the few leading causes with high malignancy, able to escape the chemical therapy and radiotherapy and result in cancer recurrence and metastasis. Discovered by the research team, the stubborn survival of cancer stem cells was related to that the epithelial-mesenchymal transition factor snail was able to activate the inflammatory cytokines IL8. Neutralizing antibody of IL8 (IL8 inhibition) applied in animal experiment could inhibit the cancer stem cells by ⅔. Professor Shih-Hwa Chiou explained that if the cancer stem cell tissue was compared to a crime syndicate, IL-8 was just the leading assistant of snail. Relevant drugs are developed and screened to inhibit IL-8 directly and achieve the effect of symptom retard.

Some studies indicate that even though we can't detect the activity of telomerase in normal body cells but can detect it in the highly-divided cells such as the stem cell and more than 80% cancer cells. Thus, it will be an optimum anticancer method to reduce the activity of cancer cell telomerase but not damage the normal stem cells. The activity of telomerase is mostly depended on the expresson level of hTERT gene (telomerase reverse transcriptase). $NF_KB$ and AP-1 can regulate the transcription of hTERT (i.e. the promoter of hTERT) positively. Discovered in recent studies, inhibition of hTERT gene expression will lead to cell death caused by the reduction of activity of non-telomerase. This is because that hTERT will affect the cell survival via p53 or PARP upon analysis. Thus besides reducing the activity of telomerase, inhibition of hTERT gene expression will also lead to cell death directly.

Carbohydrate chemistry and molecular glycobiology is one of another key issue for R & D team of Academia Sinica, Taiwan and become a significant results for them. The president Wong, Chi-Huey is good at carbohydrate technology and becomes the internal authority due to more than 30 years' studies on sugar chain (glycoprotein). *Ganoderma lucidum* polysaccharide is a very useful material recommended by him. Substances containing sugar chain (e.g. glossy *ganoderma*, β glucan and ABM, etc) are suggested by experts of Taiwan and world, for treats the carbohydrate antigens. Cells without the carbohydrate antigens are normal cells, that is, these cells without cancer cells.

People gradually learn some molecular characteristics of the cancer stem cells, such as surface molecule markers, drug resistance, radioresistance and signal channel of tumor stem cells. In 2008, Mei-Chuan Tang and Dr. Yeu Su in Institute of Biopharmaceutical Science, National Yang-Ming University published the New Dawn for Cancer Curing in Science Development. They found out the inhibition and annihilation methods against varieties of tumor stem cells and explained that selectively inhibiting the growth of and even annihilating the tumor stem cells are a possible task. In the paper, they pointed out that it would not bring bad impact on the growth and survival of normal stem cells but have the effect of inhibition and annihilation of the cancer stem cells to adopt the transcriptional factor $NF_KB$ and phosphatidylinositol 3-kinase (PI3K), mammalian target of rapamycin mTOR, bone morphogenetic protein and other strategies. In the progress to find out what ingredient has all or part of these effects, as proved by the history, the ingredients in the present invention are not cancerigenic factors. On the contrary, they have the effects of cancer prevention, anticancer and cancer curing. The main ingredients resveratrol, PPARs active agent, ginsenosides, root of red-rooted *salvia, panax* notoginseng saponins, soybean isoflavone, catechin and polysaccharide have crucial inhibition effect on the cancer cells.

(I) Nuclear transcription factor $NF_{\kappa}B$ is the bodyguard of cancer, which can activate the signal transcription channel and has important effects on immune response, inflammation, cell proliferation, cell differentiation, apoptosis and canceration. $NF_{\kappa}B$ is the main controllable factor for anti-apoptosis, which can activate the survived gene and express the survived protein. In 2008, Iyori discovered that, resveratrol could inhibit the activation of $NF_{\kappa}B$, subunit phosphorylation of $NF_{\kappa}B$ P65, nuclear translocation and transcription of $NF_{\kappa}B$-dependent report gene as well as block up $NF_{\kappa}B$ activation induced by phorbol ester, lipopolysaccharide, $H_2O_2$ and ceramide, etc. Moreover, resveratrol could inhibit both $NF_{\kappa}B$ activation and $NF_{\kappa}B$-related gene expression, which exerted functions through inhibiting $I_{\kappa}B$ kinase of $NF_{\kappa}B$ so as to block $NF_{\kappa}B$ activation and $NF_{\kappa}B$-dependent gene expression. Resveratrol, catechin, root of red-rooted *salvia* and dioscin are all the inhibitors of $NF_{\kappa}B$.

(II) The anti-tumor effect of resveratrol that was found by She QB in 2002 is closely associated with the signal transduction pathways of interference phosphatidylinositol-3-kinase (PI3K). In JB6 epidermal cells planted by using the mouse, the resveratrol and its derivatives can inhibit the conversion of tumour cells through blocking the PI3K-Akt activity transmitted by epidermal growth factors. In 2004, Pozo-Guisado E in research on human breast cancer cells found that resveratrol could impact the PI3K signal pathways related to the estrogen hormone receptor a so as to block the cells survival and proliferation, but and the process is not associated with the function of estrogen hormone receptor a.

Yu-Jhen Cheng, China Medical University, Graduate Institute of Cancer Biology (Taiwan), makes the related research on the cells metastasis of lung cancer inhibited by resveratrol in the FOXC2 (forkhead box C2) in 2009, and this conclusion shows the resveratrol could decrease the activity of PI3K/Akt-FOXC2 through using activation of Serine/Threonine and Dephosphorylation, so as to obtain inhibiting the purpose of metastasis of lung cancer cells.

In 2010, Huang Linyu in the Center of Molecular Biology (CMB), Medical College of Shantou University investigates that resveratrol inhibits EGF-induced invasion of human lung adenocarcinoma A549 cells, and this conclusion showed that 20 µM resveratrol inhibit A549 cells' invansion possibly through the suppression of the phosphorylation of ERK1/2 and PI3K-Akt signalling pathways, subsequently exerting effect on matrix metalloproteinases 2(MMP-2).

In 2010, Ye Cuilin et al. researched on the mechanism of resveratrol anti-breast cancer in the Department of Traditional Chinese Medicine of the Sixth People's Hospital Affiliated of Shanghai Jiao-Tong University, and they confirmed that resveratrol could inhibit breast cancer initiation, promotion and progression. The resveratrol might be associated with anti-inflammatory effects, restraining the activity of cytochrome enzyme P450, adjusting the levels of estrogen hormone in the initiation stage. Resveratrol might be associated with the anti-inflammatory, inhibition mechanism of cyclooxygenase-2 (COX2) and peroxidase in the promotion stage. Resveratrol might be associated with interfering the signal pathways of phosphoinositide 3-kinase (PI3K), inducing the differentitatin and apoptosis of tumor cells, inhibiting the tumor cells proliferation mechanism in the progression stage. Other mechanisms of the resveratrol against breast cancer include inhibiting angiogenesis, survivin, and the activity of BCRP/ABCG2 multidrug resistance proteins of breast cancer.

(III) In 2010, Gurusamy firstly found that low doses of resveratrol may enhance the effects of killing the cancer cells of anti-cancer drugs through inhibiting the signal pathways of target protein mTOR of rapamycin, impacting the Akt signal transduction.

(IV) In 2008, SHAO Hua-yi who works Institute of Medicinal Biotechnology, Chinese Academy of Medical Science and Peking Union Medical Collage investigates that advance of bone morphogenetic protein-2 (BMP2) and osteoporosis drugs. This experimental results show that the resveratrol might improve the activities of alkaline phosphatase, increase mineralization, and enhance the levels of type I procollagen, osteocalcin and BMP-2. SHAO Hua-yi also speculated that resveratrol might affect the synthesis and expression of BMP-2 so as to impact the activity of alkaline phosphate and osteocalcin.

In 2009, Kawei researched on to the proliferation and differentiation of rat mesenchymal stem cells affected by quercetin in Jinan University (Guangzhou City, Guangdong). This conclusion shows that quercetin might promote the proliferation and differentiation of mesenchymal stem cells of bone marrow. The differentiation mesenchymal stem cells that the quercetin could increase the expression of BMP2 mRNA.

The above contents coincided with the phenomenon of Transcription Factor $NF_{\kappa}B$ and phosphatidylinositol 3-kinase (PI3K) message transmission to abnormal activation within cancer stem cells, opinion that use the current $NF_{\kappa}B$ and PI3K inhibitor to slow its growth, opinion that inhibit the target protein mTOR of mammalian rapamycin in the phosphatidylinositol to increase the anti-cancer drugs killing cancer cells; In addition, the above contents also coincided with the Bone Morphogenetic Protein (BMP) found by scientist could promote the differentiation in vitro of GBM (glioblastoma multiforme) stem cells of CD133 positive, opinion that could decrease forming the tumour in the body of experimental animals.

(V) In 2008, Li Tan made the research on the Resveratrol Anti-hepatoma Bel-7402 and Regulation of Tumor-bearing Mice L-8 Secretion Mechanism in the Department of Immunology, Medical College of Chinese People's Armed Police Force (Tianjin, China). This conclusion indicates that the resveratrol could inhibit the tumor-bearing mice L-8 generation and inhibit the content of Mrna and protein, this conclusion also considered that the resveratrol in the outside of inside of body could exert the effective anti-hepatoma biology activity and immune regulation function.

In November 2008, Ma Yongyong made the research on the effects of resveratrol on expression and secretion of IL-8 and VEGF of Lymphoma Raji cells in The First Affiliated Hospital of Wenzhou Medical College. This conclusion indicates that the resveratrol could inhibit the proliferation of lymphoma Raji cells and IL-8 mRNA expression of lymphoma Raji cells in vitro. This research indicated that resveratrol could inhibit the endothelial cell proliferation to form new blood vessels through inhibiting IL-8, so as to inhibit the tumor growth and metastasis, and provided the theoretical basis for the clinical application of resveratrol.

In 2009, WU Xiao-jie investigate the effects of resveratrol and rutin on the secretion of interleukin-6 (IL-6) and interleukin-8 (IL-8) from human mononuclear cells (MNCs) and polymorphonuclear cells (PMNCs) following the stimulation with lipopolysaccharide (LPS) or peptidoglycan (PGN) in Institute of Antibiotics, Huashan Hospital, Fudan University in Shanghai. This conclusion indicated that the resveratrol and rutin may exert different inhibitory effects on the cytokine secretion of human MNCs and PMNCs.

The above contents coincided with Hsei-Wei Wang point of view in VGHtpe-YangMing team in 2011, the point of view is to inhibit the cancer stem cells through inhibiting the IL-8 so as to slow the symptom.

(VI) In 2009, Li Tan, who worked in the Department of Immunology, Medical College of Chinese People's Armed Police Force (Tianjin, China), made the research on Resveratrol to induce apoptosis of leukaemia cells in Acta Academiae Medicine CPAPF. The conclusion from an existing study indicated that:
1 The resveratrol can induce the apoptosis of tumor cells through regulating the cells cycle.
2. The resveratrol can facilitate the apoptosis of tumor cells through inducing the p53 expression.
3. The resveratrol can induce the apoptosis of tumor cells through Bcl-2 family.
4. The resveratrol can induce the apoptosis of tumor cells by mitochondrial pathway.
5. The resveratrol can induce the apoptosis of tumor cells through Fas-FasL signal.

In 2009, LI Yong-jun made the research on the Expression Impact of Resveratrol to Esophageal Cancer Cell Apoptosis Related Gene, Survivin and Bax in the Department of Laboratory, the Second Hospital of Hebei Medical University (Shijiazhuang, China). This conclusion indicates that the resveratrol could induce the esophageal cancer cell apoptosis, its mechanism may be related to the expression of survivin and Bax.

Survivin is an apoptosis inhibition protein which can widely express the human tumors, and it has various functions such as inhibition of cells apoptosis, involving in cells cycle regulation and promotion of blood vessel formation.

2011, YANG Kai who worked in the Department of Respiratory Medicine of First People's Hospital in Huaihua City, Hunan Province, made the research on the inhibitory effect of resveratrol on growth of Lewis lung cancer cells in mice and possible mechanism. This conclusion indicates that resveratrol has an effect of inhibiting the growth of Lewis lung carcinoma in mice, while its mechanism may be related to inhibiting the expression of MIF protein and inducing the apoptosis of cancer. MIF is a unique cell factor that can promote the occurrence of malignant tumors, and it can directly effect the fragmentation of normal cells and induce the malignant transformation of cancer genes, it can also inhibit the function of cancer gene P53, and promote angiogenesis, occurrence and development of tumors through adjusting the immunological reaction.

In May 2011, Li Yan who worked in the First Hospital Affiliated of China Medical University made the relevant research on the Impact of resveratrol to MDA-MB-231 cell apoptosis of breast cancer induced by TRAIL. This conclusion indicated that combination application between tumor necrosis factor-related apoptosis inducing ligand (TRAIL) and resveratrol could inhibit the MDA-MB-231 cell proliferation and reduce its apoptosis. In addition, the effects whose resveratrol enhanced the TRAIL to induce the cell apoptosis are achieved by promoting the expression of caspase-8 and caspase-3.

TRAIL is a cell factor that may induce the apoptosis through combining with relevant receptors to induce the apoptosis in the target cells. It can selectively kill the cancer cells, but no obvious damages to normal tissue.

In October 2011, Zhang Zhiliu who worked in the Gynecology department of Ancillary Hospital of Qingdao University Medical College made the research on the Resveratrol Inhibiting the Proliferation of Hela Cells and Its Mechanism. This conclusion indicated that the resveratrol has obvious inhibition effects on the vitro growth of cervical cancer Hela cells, and its mechanism may be related to the expression of inhibiting p-e1F4E and p-4E-BP1, inducing the activation of caspase-3 to increase the apoptosis of Hela cells.

In 2011, Yang Zheng who worked in the Stomatology Department of First Affiliated Hospital in Liaoning Medical College made the research on the Impacts and Its Mechanism of resveratrol to Proliferation and Apoptosis of Human's Oral Squamous Cell Carcinoma KB Cells. This conclusion indicated that resveratrol could inhibit the proliferation of KB cells, retard S phase to induce the apoptosis of cells. At the same time, survivin, caspase-3 and Smac gene involved in the role of resveratrol to induce the apoptosis of KB cells.

The above contents accord with the opinions of Shih-Hwa Chiou, which are to inhibit the anti-apoptotic protein of cancer stem cells to eliminate the drug resistance and radioresistance of cancer stem cells in order to completely annihilate it.

(VII) In 2004, Lin Hai who worked in the Jilin University made the research on the Experiment of Anti-tumor Effect of Resveratrol. This conclusion indicates that the resveratrol could decrease the telomerase activity in K562 cells to exert the anti-tumor effects, and take on the dose-response relationship. Lin Hai firstly considered that the resveratrol could affect the telomerase activity in tumor cells.

In 2004, Jia Xudong who worked in the Nutrition and Food Safety Institution of Chinese Center for Disease Control and Prevention made the research on the Effects of Tea Polyphenols/Tea Pigments to HepG2 Telomerase Activity of Human Hepatoma Cell Line. This conclusion indicates that the tea polyphenols and tea pigments could markedly inhibit the telomerase activity in HepG2 Cells, and the telomerase activity might be a useful biomarker in the cancer chemoprevention study.

In 2006, ZHENG Guo-hua, who worked in the Fujian University of Traditional Chinese Medicine, research on inhibitory action and its mechanism of garlic oil combined with resveratrol on human gastric cancer cell. This conclusion indicates that the combined medication of garlic oil and resveratrol could not only inhibit the proliferation of gastric cancer cells but also have the synchronizing action. Its mechanism might be associated with the gene expression of reverse transcriptase hTERT, which could inhibit the gastric cancer cells Bcl-2, c-myc and human telomerase.

In 2008, Zhang Dong-dong who worked in the Basic Medical College of Jiamusi University made the research on the Mechanism of Resveratrol Inhibiting Gastric Cancer BGC823 Cells proliferation. This conclusion indicates that after resveratrol acted on BGC823, with the extension of the time, the telomerase activity should be declined. The results indicates that the cancer cells inhibited by resveratrol drug might be associated with telomerase activity. The results analyzed by experimentation indicates that the resveratrol could inhibit the proliferation effects of human gastric cancer BGC823 cells planted by out of human body, it might be associated with cancer cells that were arrested cell cycle at S phase and activated by telomerase.

In January 2010, WANG Xiao-yan who worked in Department of Gastroenterology, the Affiliated Hospital of Jiangsu University, explored the effect of resveratrol on promoter and human telomerase reverse transcriptase (hTERT) expression of human colorectal cancer cells. This conclusion indicates that the expression of mRNA and protein of cells treated with resveratrol were down-regulated in dose- and time-dependent manner. Resveratrol may suppress telomerase activity through inhibiting expression of hTERT promoter of colorectal cancer cells.

In 2010, SHEN Rong, worked in the Affiliated Hospital of Jiangsu University, explored the effect and mechanism of resveratrol on human laryngealcarcinoma cell proliferation. This conclusion indicates that the resveratrol may suppress human laryngeal cancer Hep-2 cell proliferation through inhibiting the telomerase activity and hTERT protein expression.

In 2008, NIU Ying-cai, who worked in the Institute of Medical Sciences, Qiqihaer Medical College, explored the effect of a low molecular weight polysaccharides isolated from Agaricus Blazei Murill (LMPB) on Telomerase-RNA mRNA expression in Bel-7402 hepatocellular carcinoma (HCC) cells. This conclusion indicates that the low molecular weight polysaccharides from Agaricus Blazei Murill (LMPB) could decrease the expression of telomerase-RNA mRNA, so as to reduce the telomerase activity and inhibit the growth of cancer cells.

In 2009, LIU found that telomerase activity in the Leukemia K562 Cells was very high. When using PPARs active agent to act on K562 Cells, LIU found that PPARs active agent could activate PPARγ and reduce the telomerase activity in K562 cells. Using PPARs active agent to act on K562 Cells for 72 hours, LIU found that telomerase activity in K562 Cells closed to zero.

The researchers found that they have a variety of mechanism on inhibiting the cancer generation through research on Resveratrol, PPARs activity agent, Catechin and Agaricus Blazei Polysaccharide. In particular, they had not only transcription effects which could inhibit the Cancer cells hTERT (Telomerase transcriptase) gene, so as to cause hTERT mRNA to descend, but also the combination location of $NF_\kappa B$ and AP-1 on hTERT promoter, and they would not harm the telomerase in the normal stem cells.

(VIII) In 2007, LUD found that part of PPARγ receptor activity agents could activate PPARγ inhibition β-catenin protein expression, so as to effect β-catenin signal transduction pathways. At the same time, LUD found that PPARγ could cause apoptosis and growth inhibition of $CD133^+$ brain tumor stem cells.

(IX) In 2011, Su Zhiyun, who worked in the Neurosurgery of Lanzhou General Hospital, Lanzhou Military Region, investigate the effect of resveratrol of glioma cell line U87 and cancer stem cells (CSCs). This conclusion indicates that the resveratrol could induce apoptosis of the malignant glioma cell line U87 and cancer stem cells (CSCs).

(X) In 2012, Shih-Hwa Chiou who worked in the Medical Research and Education Department of Taipei Veterans General Hospital made the research on the isolation and cultivation technology of cancer stem cells, and treatment platforms of enhancing the radiosensitivity by resveratrol. This conclusion indicates that the polyphenol compound resveratrol could inhibit the self-renewal capacity of cancer stem cells after selecting a variety of substances. The high concentration of resveratrol could also enhance the radiosensitivity through using mice bearing tumor in experiment, so as to enhance 30%-50% of radiotherapy, and one-third of cancer stem cells survival. Mice's survival period could be extended from two months to four months, so mice's survival period has doubled.

The above contents are the new example for natural ingredients, which can inhibit the cancer/tumor stem cells. The present invention will combine it into a new formula to achieve the anticipated effects.

The above content is only example. Any spirit and scope that did not separate the intention, which is modified and changed, shall contain in the attached application patent scope.

The above description should be considered as only the discussion of the preferred embodiments of the present invention. However, a person skilled in the art may make various modifications to the present invention. Those modifications still fall within the spirit and scope defined by the appended claims.

The invention has been described with reference to various specific and preferred embodiments and techniques. However, it should be understood that many variations within the spirit and scope of the invention.

What is claimed is:

1. A food composition for nourishing, maintaining and cultivating stem cells, wherein the stem cells include hematopoietic stem cells, mesenchymal stem cells, endothelial precursor stem cells, neural stem cells, retinal stem cells and cochlear stem cells, the food composition comprising: either grape skin containing resveratrol or *polygonum cuspidatum* root extract containing resveratrol, wherein the grape skin or the *polygonum cuspidatum* root extract is present in an amount of about 80 to 150 mg in relation to the whole food composition; *pseudo-ginseng* extract containing resveratrol, peroxidase proliferation activated receptor (PPARs) activator and *panax* notoginseng saponin, wherein the *pseudo-ginseng* extract is present in an amount of about 45 to 90 mg in relation to the whole food composition; cooked *polygonum multiflorum* thunb extract containing resveratrol, peroxidase proliferation activated receptor (PPARs) activator and blood serum, wherein the cooked *polygonum multiflorum* thunb extract is present in an amount of about 5 to 20 mg in relation to the whole food composition; *salvia miltiorrhiza* bunge extract containing resveratrol, peroxidase proliferation activated receptor (PPARs) activator, danshensu, tanshinone and protocatechuic Acid, wherein the *salvia miltiorrhiza* bunge extract is present in an amount of about 45 to 90 mg in relation to the whole food composition; blueberry extract containing resveratrol, peroxidase proliferation activated receptor (PPARs) activator, anthocyanin, proanthocyanidins, ellagic acid and red sandalwood Qi, wherein the blueberry extract is present in an amount of about 20 to 35 mg in relation to the whole food composition; bitter melon extract containing peroxidase proliferation activated receptor (PPARs) activator and triterpenoids, wherein the bitter melon extract is present in an amount of about 5 to 20 mg in relation to the whole food composition; soybean extract containing peroxidase proliferation activated receptor (PPARs) activator, wherein the soybean extract is present in an amount of about 5 to 20 mg in relation to the whole food composition; *ginseng* extract containing peroxidase proliferation activated receptor (PPARs) activator, *ginseng* saponin and *ginseng* polysaccharide, wherein the *ginseng* extract is present in an amount of about 30 to 60 mg in relation to the whole food composition; *rhodiola* extract containing peroxidase proliferation activated receptor (PPARs) activator, *rhodiola* polysaccharides and salidroside, wherein the *rhodiola* extract is present in an amount of about 40 to 80 mg in relation to the whole food composition; yam extract containing peroxidase proliferation activated receptor (PPARs) activator and dioscin, wherein the yam extract is present in an amount of about 5 to 20 mg in relation to the whole food composition; licorice extract containing peroxidase proliferation activated receptor (PPARs) activator and glycyrrhizin, wherein the licorice extract is present in amount of about 5 to 20 mg in relation to the whole food composition; *pueraria* extracts containing peroxidase proliferation activated receptor (PPARs) activator and puerarin, wherein the *pueraria* extract is present in an amount of about 35 to 65 mg in relation to the whole food composition; brown algae extract containing peroxidase proliferation activated receptor (PPARs) activator, fucoidan and sodium alginate, wherein the brown algae extract is present in an amount of about 25 to 50 mg in relation to the whole food composition; green algae extract containing peroxidase proliferation activated receptor (PPARs) activator and phycocyanin, wherein the green algae extract is present in an amount of about 25 to 45 mg in relation to the whole food composition; chuanxiong extract containing ligustrazine and sodium ferulate, wherein the chuanxiong extract is present in an amount of about 35 to 70 mg in relation to the whole food composition; green tea extract containing EGCG catechin, wherein the green tea extract is present in an amount of about 20 to 40 mg in relation to the whole food composition; apple extract containing quercetin, wherein the apple extract is present in an amount of about 25 to 45 mg in relation to the whole food composition; leek seed extract containing taurine, wherein the leek seed extract is present in an amount of about 10 to 30 mg in relation to the whole food composition; wolfberry extract containing zeaxanthin and *lycium barbarum* polysaccharides, wherein the wolfberry extract is present in an amount of about 50 to 95 mg in relation to the whole food composition; pot marigold extract containing lutein, wherein the pot marigold extract is present in an amount of about 20 to 35 mg in relation to the whole food composition; *ganoderma lucidum* extract containing *ganoderma lucidum* spores, *ganoderma lucidum* polysaccharides and amino-adipic acid, wherein the *ganoderma lucidum* extract is present in an amount of about 20 to 35 mg in relation to the whole food composition; caterpillar fungus extract containing cordyceps polysaccharide, wherein the caterpillar fungus extract is present in an amount of about 10 to 30 mg in relation to the whole food composition; *agaricus* blazei murill extract containing *agaricus* blazei polysaccharide, wherein the *agaricus* blazei murill extract is present in an amount of 5 to 20 mg in relation to the whole food composition; cistanche deserticola extract containing blood serum, wherein the cistanche deserticola extract is present in an amount of about 10 to 30 mg in relation to the whole food composition; mushroom extract containing mushroom polysaccharide, carnosine and amino-adipic acid, wherein the mushroom extract is present in an amount of about 5 to 20 mg in relation to the whole food composition; beer yeast containing yeast *beta*-1, 3/1, 6 glucan, wherein the beer yeast is present in an amount of about 10 to 40 mg in relation to the whole food composition; flaxseed oil powder containing DHA and alpha lipoic acid, wherein the flaxseed oil powder is present in an amount of about 5 to 40 mg in relation to the whole food composition; and vitamin is present in an amount of about 5 to 10 mg in relation to the whole food composition, wherein the grape skin containing resveratrol or the *polygonum cuspidatum* root extract containing resveratrol is embedded into hydroxypropyl-β-cyclodextrin to form an inclusion compound.

2. The food composition as claimed in claim 1, wherein the amount of resveratrol is approximately 42 wt % of the grape skins or the *polygonum cuspidatum* root extract, the *pseudo-ginseng* extract the cooked *polygonurn multiflorum* thunb extract, the *salvia miltiorrhiza* bunge extract and the blueberry extract; the amount of peroxidase proliferation activated receptor (PPARs) activator is approximately 28 wt % of the *ginseng* extract, the *pueraria* extract, the *rhodiola* extract, the brown algae extract, the green algae extract, the soybean extract, the yam extract and the licorice extract; the amount of EGCG catechin is approximately 90 wt % of the green tea extract; the amount of quercetin is approximately 80 wt % of the apple extract; the amount of polysaccharides is approximately 20 wt % of the *ginseng* extract, the wolfberry extract, the *rhodiola* extract, the *ganoderma lucidum* extract, the caterpillar fungus extract, the mushroom extract, the *agaricus* blazei murill extract and the yeast *beta*-1, 3/1, 6 glucan; the amount of *ginseng* saponin is approximately 30 wt % of the *ginseng* extract; the amount of *panax* notoginseng saponin is approximately 30 wt % of the *pseudo-ginseng* extract; the amount of lutein is approximately 80 wt % of the pot marigold extract; the amount of zeaxanthin is approximately 25 wt % of the wolfberry extract; the amount of tanshinone, danshensu, protocatechuic acid is approximately 27 wt % of the *salvia miltiorrhiza* bunge extracts; the amount of ligustrazine is approximately 50 wt % of the chuanxiong extract; and the amount of sodium ferulate is approximately 30 wt % of the chuanxiong extract; the amount of puerarin is approximately 70 wt % of the *pueraria* extract; the amount of salidroside and *rhodiola* polysaccharides is approximately 30 wt % of the *rhodiola* extract; the amount of *ganoderma lucidum* spores and *ganoderma lucidum* polysaccharides is approximately 30 wt % of glossy the *ganoderma lucidum* extract; the amount of blood serum is approximately 60 wt % of the cooked *polygonum multiflorum* thunb extract and the cistanche deserticola extract; the amount of fucoidan and sodium alginate is respectively 40 wt % of the brown algae extract; the amount of blood serum is approximately 60 wt % of the cooked *polygonum multiflorum* thunb extract and the cistanche deserticola extract; the amount of phycocyanin is approximately 10 wt % of the green tea extract; the amount of taurine is approximately 70 wt % of the leek seed extract; and the amount of DHA is approximately 80 wt % of the flaxseed oil powder extract 5 wt % of the green algae extract.

3. The food composition as claimed in claim 1, wherein the food composition is in a form of powders, particulates or liquid, and the food composition further comprises a pharmaceutically acceptable excipient, wherein the pharmaceutically acceptable excipient is selected from a group comprising free spice, sweetener, preservatives, antioxidants, chelating agent, osmotic agent, lubricants, tablet adjuvant, coloring agent, humectant, anchoring agent, and pharmaceutically compatible carrier, and the food composition is made into a capsule, a tablet, a pastille, an aluminum foil bag or a bottle.

* * * * *